United States Patent
Howlett (10) Patent No.: US 6,264,902 B1
(45) Date of Patent: *Jul. 24, 2001

(54) INSTRUMENT STERILIZATION CONTAINER HAVING AN IMPROVED LATCHING MECHANISM

(75) Inventor: Charles Howlett, Laguna Beach, CA (US)

(73) Assignee: Johnson & Johnson Medical, Inc., Arlington, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/671,980

(22) Filed: Jun. 28, 1996

(51) Int. Cl.$^7$ ........................................................ A61L 2/00
(52) U.S. Cl. ............................................ 422/300; 422/292
(58) Field of Search .............................. 206/439; 422/292

(56) References Cited

U.S. PATENT DOCUMENTS

| 4,798,292 | * | 1/1989 | Hauze | 206/439 |
|---|---|---|---|---|
| 4,915,913 | | 4/1990 | Williams et al. | 422/119 |
| 5,098,676 | * | 3/1992 | Brookes, Jr. | 422/292 |
| 5,356,017 | * | 10/1994 | Rohr et al. | 215/216 |
| 5,451,379 | * | 9/1995 | Bowlin, Jr. | 422/297 |
| 5,518,115 | | 5/1996 | Latulippe | 206/320 |
| 5,525,314 | | 6/1996 | Hurson | 422/300 |

FOREIGN PATENT DOCUMENTS

| 3442835 | 6/1986 | (DE) . |
| 3544341 | 6/1987 | (DE) . |
| 0 331 492 A2 | 6/1989 | (EP) . |
| WO 94/08623 | 4/1994 | (WO) . |

* cited by examiner

*Primary Examiner*—Laurie Scheiner
*Assistant Examiner*—Jeffrey S. Parkin
(74) *Attorney, Agent, or Firm*—Andrew C. Farmer (57) ABSTRACT

A sterilization container for sterilizing, storing and transporting instruments is provided with a base portion having a plurality of drainage wells. The drainage wells comprise a downwardly sloping surface terminating in a drainage aperture. Upper portions of the sloping surfaces support a flexible instrument holding mat within the container. Sterilization containers are formed of thermoplastic liquid crystal polymer, such as a wholly aromatic polyester. A latch mechanism comprises a latch member rotatably supported upon torsion bars within a recessed portion of the container which presents no sharp surfaces to the user.

10 Claims, 6 Drawing Sheets

INSTRUMENT STERILIZATION CONTAINER HAVING AN IMPROVED LATCHING MECHANISM

BACKGROUND

1. Field of the Invention

This invention relates to a sterilization container for use in sterilizing, storing and transporting and presenting instruments, in particular medical instruments.

2. Background of the Invention

Most, reusable medical instruments require sterilization before each use. Many methods are employed for sterilization, but the most prevalent methods include: steam autoclaving, vapor phase chemical sterilization and vapor phase chemical sterilization in combination with a plasma field. The chemical sterilants include hydrogen peroxide and ethylene oxide. One of the most versatile, quickest and most effective methods employs an initial period of vapor phase hydrogen peroxide followed by application of an electromagnetic field which drives the hydrogen peroxide vapor into the plasma state of matter. The plasma phase enhances the sterilization and when the electromagnetic field is released the plasma free radicals recombine to form water and oxygen.

Typically, instruments are placed into a container and then the container is placed into the sterilization device. Portals for the passage of sterilizing media must be provided. Also, the container is usually provided with a filter material which allows passage of the sterilizing media through the portals and container yet prevents the ingress of microorganisms. The portal and filter material may be combined as in the Nichols U.S. Pat. No. 4,704,254, issued Nov. 3, 1987 and incorporated herein by reference, or the container may be provided with a plurality of apertures and then be wrapped prior to each sterilization in a filter wrapping material such as SPUNGUARD brand CSR wrap available from Kimberly Clark Corporation which is a spunbonded/meltblown/spunbonded (SMS) laminate consisting of nonwoven outer layers of spun-bonded polyolefins and an interior barrier layer of melt-blown polyolefins.

Usually, holding devices of one form or another hold one or more individual instruments within the container. The holding device may comprise clips or other such arrangements, which may or may not be specially adapted to hold a particular medical instrument. One popular holding device simply comprises a plurality of upwardly extending flexible projections, sometimes called fingers, which prevent the instruments from moving about within the container and provide minimal contact with the instruments. Typically, these are provided on a mat which lies in the bottom of the container.

To keep costs low and to prevent interference with an electromagnetic field in some sterilization processes, it is desirable to form a sterilization container from a polymeric material. Certain preferred polymers are disclosed herein. A latching mechanism for holding a cover, lid or other closure device to the rest of the container is frequently formed along with the container in an injection molding operation or affixed afterward in a simple gluing or polymeric welding operation. Typically, such latches have some exposed sharp edges which can catch on a user's glove and puncture it. Especially if the user is left unaware of the glove damage, the user could be exposed to harmful pathogens.

SUMMARY OF THE INVENTION

The present invention overcomes these and other limitations in the prior art and provides compatibility with hydrogen peroxide vapor, liquid or gas plasma, steam autoclaves, ethylene oxide and other chemical or heat based sterilizing methods. It is durable, inexpensive to produce, enhances drainage and limits condensate entrapment.

A sterilization container according to the present invention for sterilizing instruments comprises a tray having at least one port for passing sterilizing media into and out of the tray, means for holding a medical instrument within the tray, and an outer tray wall portion. A lid, having an outer lid wall portion, is moveable with respect to the tray for providing access to the tray and a latching mechanism releasably connects the lid to the tray. The improvement of the present invention comprises a recessed portion in either the tray outer wall portion or the lid outer wall portion which forms a latch recess. The latching mechanism is entirely received within said recess whereby no portion of the latching mechanism extends laterally of the recess, thereby reducing the chance that the latching mechanism might catch and puncture a thin protective glove of a user.

The latch recess may further comprise opposing side walls with a latch member rotatably mounted within the latch recess for rotation about an axis. An engagement surface is formed on the other of the tray outer wall portion and lid outer wall portion. The latch member has an engagement lip engageable with the engagement surface. An actuation surface on the latch member is removed from its axis of rotation whereby a force applied to the actuation surface urges the latch member away from the engagement surface and the engagement lip away from the engagement surface. Preferably, such force is applied in a direction inwardly of the latch recess. Preferably, the latch member is rotatably mounted upon a torsion member extending inwardly of the latch recess from the opposing sidewalls, the torsion member biasing the latch member into a standing position about said axis. To minimize glove punctures while using the latch mechanism, preferably the engagement lip is disposed on an inwardly facing portion of the latch member with an outwardly facing portion being free of sharp edges.

DETAILED DESCRIPTION

Figure 1:
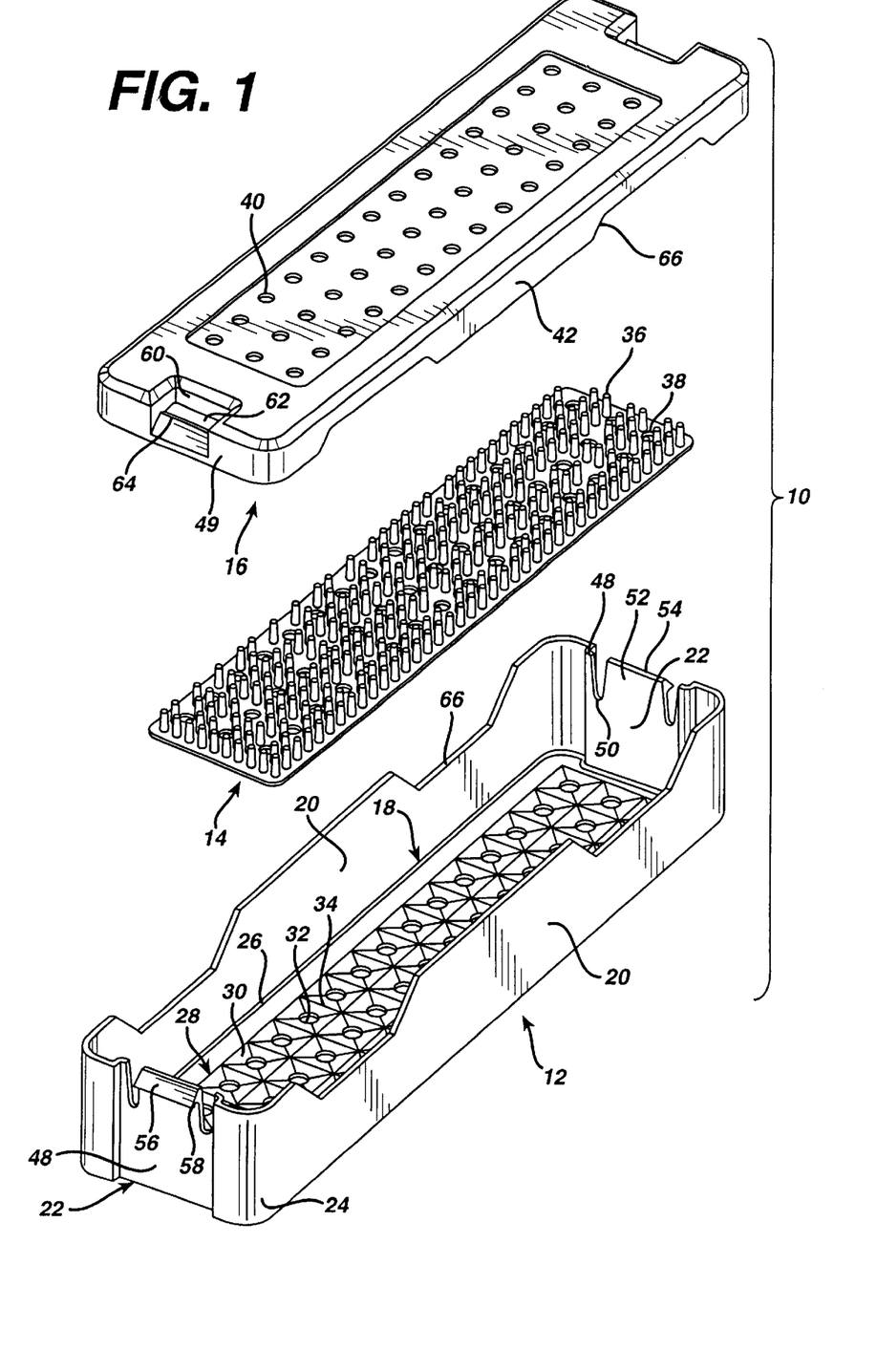
FIG. 1 is an exploded, perspective view of a sterilization container according to the invention.

FIG. 1 illustrates a first embodiment of a sterilization container 10 according to the present invention. The container 10 comprises a tray 12, a mat 14, and a lid 16. The tray 12 comprises a rectangular base 18 from which extends upwardly two opposing side walls 20 and two opposing end walls 22. Corners 24 formed between the side walls 20 and end walls 22 are rounded for a pleasing appearance, improved strength, and to reduce sharp edges which may compromise the integrity of an operator's protective rubber glove (not shown). A fillet 26 between the base 18 and the side and end walls 20 and 22 also enhances the strength of the tray 12.

The base 18 comprises a plurality of drainage wells 28, each one comprising a downwardly sloping surface 30 terminating in a drainage aperture 32. The sloping surfaces 30 of adjacent drainage wells 28 intersect to form peaks 34. Preferably, the peaks 34 form distinct lines or singularities, as opposed to rounded interfaces between adjacent sloping surfaces 30. This minimizes the surface areas of the peaks 34 which support the mat 14, thereby reducing the area of contact between the base 18 and mat 14. Thus, little space is provided in which condensate or other liquid matter may become trapped.

The mat 14 has a plurality of mat apertures 38 therethrough and a plurality of upwardly extending projections 36 for holding medical instruments (not shown) that are to be sterilized within the container 10. Apertures 38 on the mat 14 align with drainage apertures 32 through the tray base 18. Preferably, the mat 14 is formed of a silicone or other elastomeric substance which resists high heat associated with steam autoclaving, and also resists chemical attack from hydrogen peroxide, ethylene oxide, or other chemical sterilants or their precursors, particularly the oxidizing type sterilants. Further, the material of the mat 14 should not absorb or chemically interact with such chemical sterilants.

The upwardly extending projections 36 may take several forms. For instance, they may taper upwardly, or have constant diameter. The tip may be flat, rounded or radiused. They may be relatively soft or they may be rigid. The total number and spacing of the projections 36 may also be varied. Such mats are known in the art, and it is well within the ordinary skill of a practitioner in the art to vary these design parameters to achieve a desired overall effect.

The container lid 16 has a plurality of lid apertures 40 to promote the passage of sterilizing vapors therethrough. The lid apertures 40 may align with the drainage apertures in the tray 12, but need not be so aligned. The lid 16 further comprises downwardly depending sidewalls 42 and endwalls 44.

Figures 2, 3:
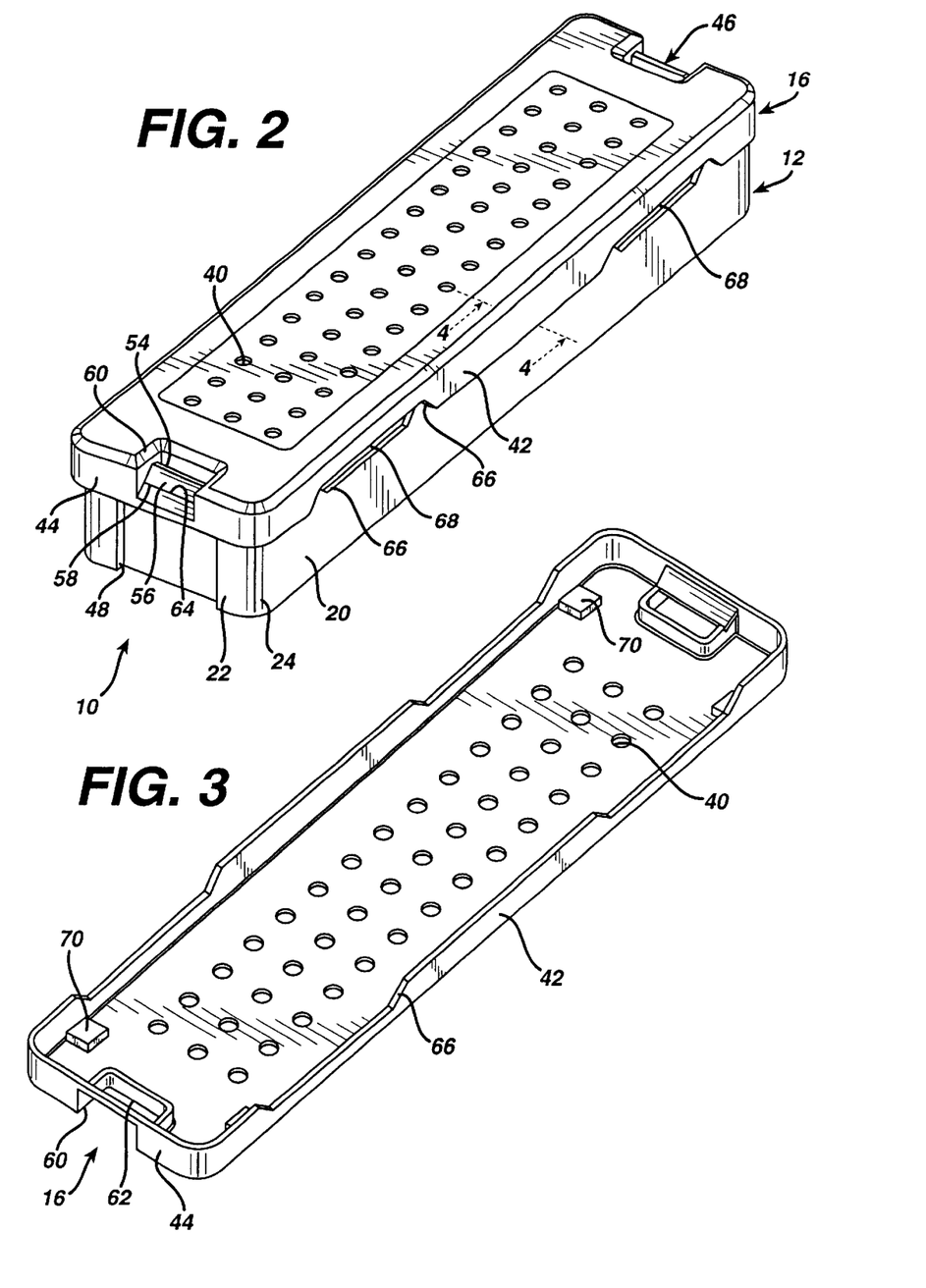
FIG. 2 is a perspective view of the assembled sterilization container of FIG. 1.
FIG. 3 is a perspective view of the inverted lid of the sterilization container of FIG. 1.

Turning also now to FIG. 2, the tray 12 and lid 16 are sized so that the tray endwalls or sidewalls and endwalls 20 and 22 fit snugly within the lid sidewalls and endwalls 42 and 44. Preferably, a latching mechanism 46 is integrally formed in the tray 12 and lid 16. Each of the base endwalls 22 has a recessed portion 48. A pair of U-shaped cutouts 50 in each recess portion 48 define a flexible tang 52. An upper extent 54 of each tang 52 comprises a sloped camming surface 56 and a retaining lip 58. Recessed portions 60 in the lid 16 align with the endwall recesses 48 and comprise an aperture 62 and retaining lip 64. To engage the latch mechanism 46, the camming surface 56 on each tang 52 is inserted into the corresponding aperture 62 in the lid 16 and cammed over the retaining lip 64 until the retaining lip 58 on the tang 52 snaps into engagement with the retaining lip 64. Inward pressure on the tang 52, applied manually, disengages the retaining lips 58 and 64 to release the latch mechanism 46.

To enhance the flow of sterilizing gases through the container 10, each of the tray sidewalls 20 and lid sidewalls 42 contain several shallow cutout portions 66. As best seen in FIG. 2, when the lid 16 and tray 12 are interconnected, the cutout portions 66 thereon align with each other to form shallow slit-like openings 68 into the container 10. This enhances the flow of sterilizing gases through the container 10.

Turning to FIG. 3, four pads 70 are provided inside of the lid 16 to space the lid 16 from the tray 12 and thereby minimize any surface contact area therebetween which might block the flow of gas or liquid or which might trap, condensate, or other liquid material.

Figure 4:
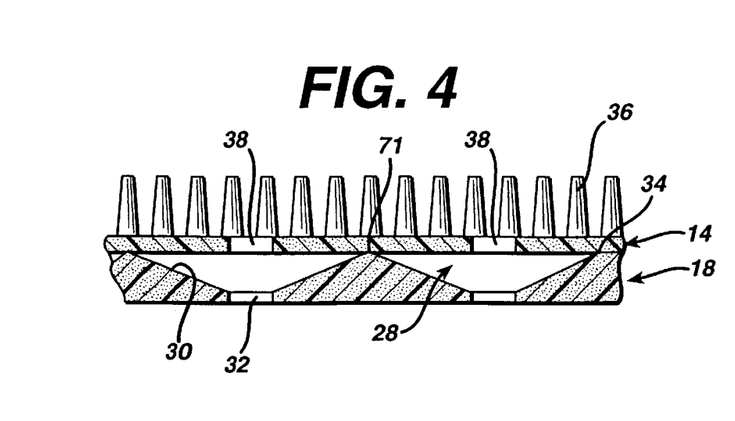
FIG. 4 is a cross-section taken along lines 4—4 of FIG. 2.

FIG. 4 illustrates the drainage enhancing features of the present invention. The peaks 34 of the base 18 support the flexible mat 14. Condensate or other liquid which enters between the mat 14 and base 18 comes within one of the drainage wells 28. The small contact surface 71 formed between the peaks 34 and mat 14 prevents condensate or other liquids from being trapped between surfaces of the base 18 and mat 14. The downwardly sloping surfaces 30 of the drainage wells 28 encourage any condensate or other liquids to move toward the drainage apertures 32. Condensate then physically drains out of the container 10. The supporting characteristics of the peaks 34 can not be over emphasized. Silicone and other elastomeric materials suitable for forming the mat 14 tend to soften considerably in high temperature sterilizing environments. Accordingly, it is crucial to properly support the mat 14.

The selection of tray material for use in hydrogen peroxide or chemical based sterilization technology is influenced by the chemical resistance and inertness of the material with respect to the sterilant or precursor for chemical plasma. For chemical plasma sterilization methods which depend on excited free radicals, the inertness of the material with respect to the plasma precursor is even more critical due to possible low concentrations of precursor available to generate plasma in some preferred plasma methodologies. The tray material should be non-reactive to the sterilant(s), or the precursor(s) for the chemical plasma in order not to affect biological lethality of the sterilizer chamber. For ease of operation, the material should also be resistant to the chemical and thermal environments during the cleaning and decontamination procedure of instruments and trays as commonly used in clinical situations. Hospitals typically use a washer/decontaminator operating at 270° F. as well as detergents and enzymatic cleaners for removing organic matter.

The ideal tray material should further be compatible with all major sterilization methods employed by hospitals and the like, including steam (flash and gravity), ethylene oxide gas, and hydrogen peroxide based sterilizers. One example of the hydrogen peroxide based plasma sterilization is the STERRAD Sterilization System that uses hydrogen perox- ide plasma to eliminate microorganisms on medical instruments. Therefore, the ideal material should have adequate thermo-mechanical properties to withstand steam, exhibit low ethylene oxide residuals after processing, and have extremely low interaction with $H_2O_2$ or other oxidative sterilants.

We have rigorously examined and tested many materials to identify a material suitable for such varied and extreme service environments. As a result of our investigations, we have found the preferred materials to be neat (non-reinforced) and reinforced polyester based liquid crystal polymers, neat and reinforced polyesters, and reinforced polypropylene. The most preferred material is neat or reinforced polyester liquid crystal polymer, or its blend with the above mentioned polymers. One commercially available example of a suitable liquid crystal polymer is the Vectra® family produced by the Hoechst Celanese Corporation.

Within each family group, there are preferred chemical structures, either with or without reinforcement, which can be considered as tray materials:

I. Reinforced polypropylene, especially when reinforced with calcium carbonate or glass fiber, provides the chemical inertness and structural properties required for multi-sterilization application.

II. Polyester type polymers have a variety of basic structures, among them:
1. Polyethylene terephthalate (PET) with the following chemical structure:

2. Polybutylene terephthalate (PBT), in which chemical structure is:

and

3. Polycyclohexylene terephthalate (PCT), with the following chemical structure:

PCT is available from Eastman Chemical Company under the tradename of "Ektar", in a variety of unmodified and modified structures. Modification may include acids and glycol structures.

Among the polyester family, the structure of polyethylene terephthalate is preferred. The most preferred configuration is glass fiber reinforced PET. The fiber reinforcement provides structural strength for steam autoclave operation and is preferred in oxidative chemical vapor or oxidative chemical plasma sterilization methods.

III. Liquid crystal polymers, in which there are four major structural variations:
1. Polybenzoate-naphthlate

An example of a commercially available product is under the tradename VECTRA® and C series by Hoechst Celanese Corporation.

2. Polybenzoate-terephthalate-bis phenol-isophthalate

An example of a commercially available product is under the tradename of Xydar® by Amoco Performance Products.

3. Polybenzonate-terephthalate-ethylene glycol

An example of a commercially available product is under the tradename of X7G and X7H by Eastman Chemical Company and 4. Polynaphthalate-amino terephthalate An example of a commercially available product is under the tradename of Vectra® B series by Hoechst Celanese Corporation.

The most preferred structures are the wholly polyester aromatic liquid crystal polymers, which are polybenzoate-naphthalate and polybenzoate-terephthalate-bis phenol-isophthalate. Both neat and reinforced grades are preferred due to the structural strength of this material family. The most preferred reinforcements fillers are glass or mineral fibers, or fluoropolymers in powders.

The material characteristics in a hydrogen peroxide environment are of particular importance. Both the tendency to absorb hydrogen peroxide and the tendency to decompose hydrogen peroxide were studied for a variety of materials. The following Table 1 illustrates the results for some of the more important materials.

TABLE 1

| Material Tradename | Material Family | H$_2$O$_2$ Absorption (ppm) | H$_2$O$_2$ Decomposition (g/g) |
|---|---|---|---|
| Ultem 1000 | Polyetherimide | 144.3 | |
| Ultem CRS 5011 | Polyetherimide | 346 | |
| Radel R-5100 | Polyaryl sulfone | 356 | |
| Noryl | Polyphenylene oxide/Polystyrene blend | 52 | |
| Vectra A530 | Polyester liquid crystal polymer (mineral fiber filled) | 4.5 | 0.009 |
| Vectra A115 | Polyester liquid crystal polymer (glass fiber filled) | no absorption | 0.013 |
| DPP40W18357 | 40% calcium carbonate filled polypropylene | no absorption | 0.012 |
| Ektar EG-015 | Glass fiber filled poly ethylene terephthalate | 3.3 | no decomposition |

Another study was conducted to evaluate the compatibility of tray materials with simulated hydrogen peroxide plasma sterilization and washer/decontamination cycles, which includes alternating hydrogen peroxide plasma sterilization cycle, washer/decontaminator cycle and enzymatic cleaner immersion. The samples were placed under 0.5% and 0.75% strain. The following Table 2 illustrates the results of this evaluation.

TABLE 2

| Material | Strain Level | Yield Strength | Tensile Strength | Elongation at Break |
|---|---|---|---|---|
| Ultem 1000 | Control | 15,320 psi | 14,690 psi | 68.5% |
| Ultem 1000 | 0.5% | 10,140 psi | 10,140 psi | 2.4% (a) |
| Ultem 1000 | 0.75% | 11,630 psi | 11,230 psi | 4.2% (a) |
| Noryl | Control | 9,965 psi | 7,852 psi | 13.1% |
| Noryl | 0.5% | 10,400 psi | 7,961 psi | 9.3% |
| Noryl | 0.75% | 10,550 psi | 8,091 psi | 98.5% |
| Vectra A530 | Control | n/a | 22,672 psi | n/a |
| Vectra A530 | 0.5% | n/a | 22,371 psi | n/a |
| Vectra A530 | 0.75% | n/a | 22,431 psi | n/a |
| Vectra A115 | Control | n/a | 24,265 psi | n/a |
| Vectra A115 | 0.5% | n/a | 23,266 psi | n/a |
| Vectra A115 | 0.75% | n/a | 23,485 psi | n/a |
| DPP40WI | Control | 3,258 psi | 2,699 psi | 19.27% |
| DPP40WI | 0.5% | 2,862 psi | 2,449 psi | 54.42% |

Aside from using chemically inert material, there are other controlling characteristics of sterilization trays or containers so as to reduce interaction with the sterilization environment and so as to enhance the resistance to hospital-use cleaning chemicals. Interaction of tray material with the sterilants or precursor for chemical plasma reduces the available sterilant or precursor for chemical plasma in vapor phase so as to effect the biological lethality. Resistance to hospital-use chemicals will lengthen the expected product life. The first characteristic to be controlled is the surface smoothness of final product. The surface of the sterilization tray should be as smooth as possible so as to reduce surface area/volume ratio. Since both chemical and physical interactions with sterilants or precursor(s) for chemical plasma and material degradation are a function of the surface area/volume ratio, smooth surfaces will reduce the rate of these interactions.

The second characteristic to be controlled is wall thickness. Wall thickness is integral to the structural strength of the tray or container. For the sterilization tray or container to operate in an oxidative chemical vapor or chemical plasma environment, often under reduced pressure and low concentration, the condensation of chemical sterilant or precursor for chemical plasma should be minimized. Condensation is a function of the thermal mass and heat transfer characteristics of the tray or container, which may reduce the amount of available sterilant or precursor for chemical plasma in vapor phase and thereby effect the biological lethality. To minimize the thermal mass and enhance the heat transfer characteristics, the wall thickness of the tray or container should be minimized.

Accordingly, the preferred materials for forming the tray 12 and lid 16 are as follows:

I. Reinforced polypropylene: Reinforced polypropylene, especially when reinforced with calcium carbonate or glass fiber, will provide the thermo-mechanical structural integrity required for multi-sterilization application.

II. Neat or reinforced polyester: Among the polyester family, the structure of polyethylene terephthalate is preferred. The most preferred configuration is glass reinforced polyethylene terephthalate (PET). The fiber reinforcement provides structural strength for steam autoclave operation and allows for a thin-wall design, which is preferred in oxidative chemical vapor sterilization method.

III. Neat or reinforced liquid crystal polymer, and/or a blend of the above materials. The most preferred structures are the wholly polyester aromatic liquid crystal polymer, which can be of the chemical structure of polybenzoate-naphthalate or polybenzoate-terephthalate-bis phenol-isophthalate. Both neat and reinforced grades are preferred due to the thermo-mechanical strength of this material family. The most preferred reinforcements types are glass and mineral fibers.

IV. A blend or alloy of liquid crystal polymers and I or II of the above.

Figure 5:
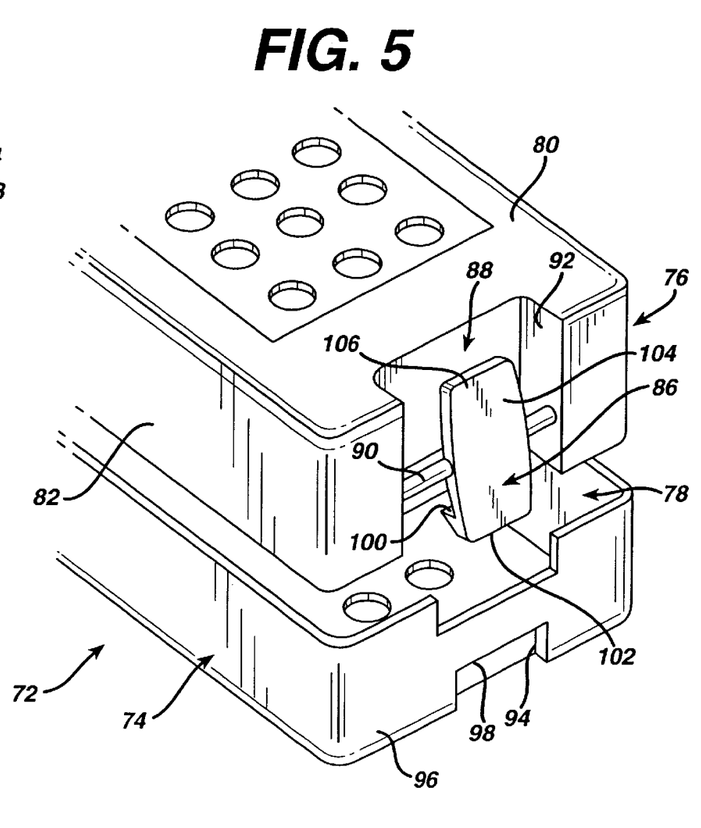
FIG. 5 is a perspective, disassembly view of a portion of a sterilization container according to the present invention which illustrates an alternative latching mechanism according to the present invention.
Figure 6:
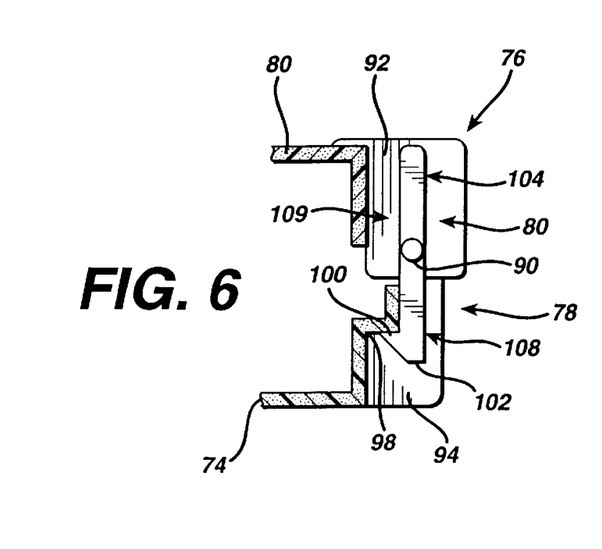
FIG. 6 is a cross-section of the latching mechanism of FIG. 5, with the latch shown in the closed position.

FIGS. 5 and 6 illustrate a second embodiment of a sterilization container according to the invention. The container 72 comprises a tray 74, lid 76 and mat (not shown) similar to the previous embodiment. However, it incorporate an alternative latching mechanism 78.

The lid 76 comprises an apertured top wall 80; side and endwalls 82 and 84, respectively, depending therefrom. A latch member 86 is integrally molded into a recessed portion 88 in each endwall 84 of the lid 76. A pair of torsion bars 90 extend inwardly of the recess portion 88 from opposing sidewalls 92 thereof to rotatably support the latch member 86. The torsion bars 90 bias the latch member 86 into a standing, engaged position as shown best in FIG. 6, and allow a limited amount of rotation away from the engaged position.

A notch 94 in each endwall 96 of the tray 74 forms an engagement surface 98. A lip 100 protruding from a lower portion 102 of the latch member 86 engages the engagement surface 98 on the tray 74 to thereby hold the lid 76 securely to the tray 74. Finger pressure against an actuation surface 104 on an upper portion 106 of the latch member 86 pivots the latch member 86 about the torsion bars 90 to disengage the engagement surface 98 from the lip 100 and thereby release the lid 76 from the tray 74. When the pressure on the actuation surface 104 is release, the torsion bars 90 return the latch member 86 to its standing, engaged position.

All edges and surfaces of the latch member 86 are rounded and smooth especially those on that portion 108 of the latch member facing outwardly of the recess 88. The only exception is the lip 100 which lies on that portion 109 of the latch member facing inwardly of the tray 74, to thereby present no sharp edges or surfaces which may engage and tear the users protective glove (not shown). All portions of the latching mechanism 78 are integrally molded with either the tray 74 or lid 76 thereby reducing manufacturing and assembly costs. Of course, the orientation of the latching mechanism 78 may be reversed, such that the latch member 86 is formed in the tray 74. Further, the lid 76 could be adapted to pivot about a hinge (not shown) and of course, the latching mechanism 78 need not be provided in the endwall 84 but could be located elsewhere on the container 72. However, the orientation illustrated in FIG. 5 is particularly convenient.

Figure 7:
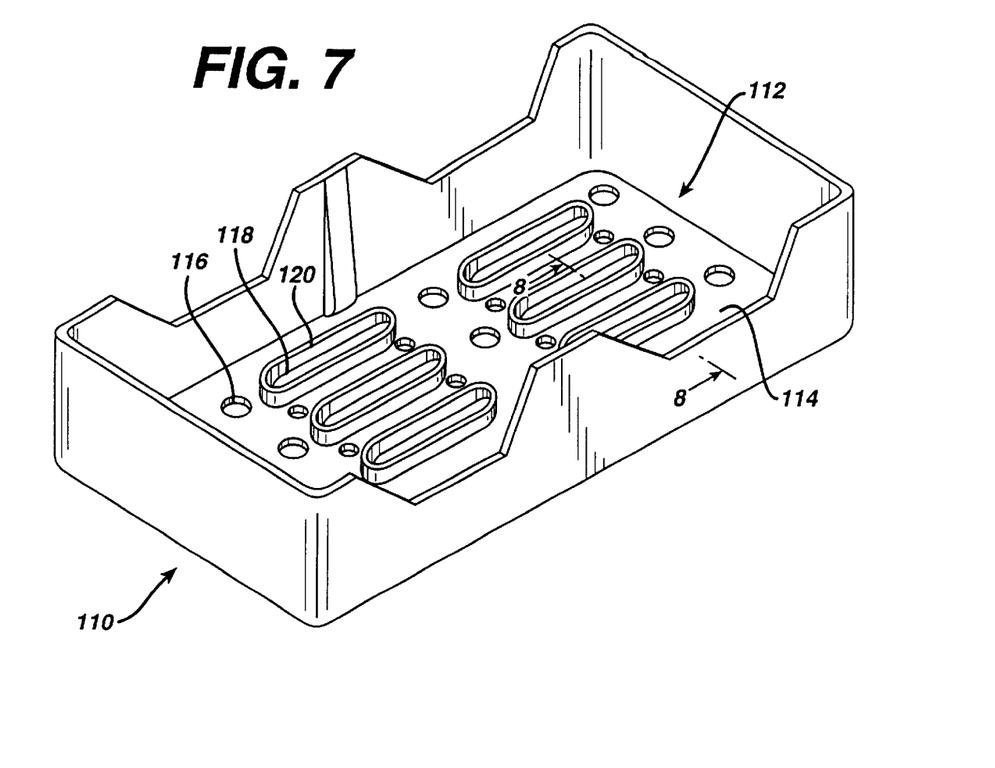
FIG. 7 is a perspective view of a further embodiment of a sterilization tray according to the present invention.
Figure 8:
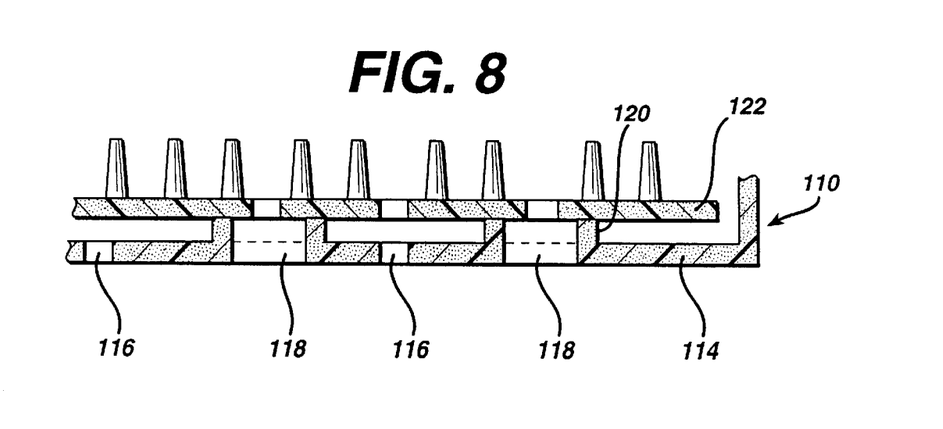
FIG. 8 is a cross-section taken along line 8—8 of FIG. 7.

FIGS. 7 and 8 illustrate an alternative arrangement for a tray 110 according to the invention. The tray 110 may be used with a sterilization container as in the first and second embodiment and differs primarily in its base 112. The base 112 comprises a flat panel 114 having a plurality of apertures 116 therethrough. Additionally, a number of larger, elongated apertures 118 penetrate the panel 114 and an upwardly extending lip 120 encircles each of the elongated apertures 118. The lips 120 support a mat 122 and further provide rigidity to the tray base 112. Apertures 124 through the mat 122 aligned with the elongated apertures 118 through the tray base 112 to provide an efficient diffusion path for sterilizing gases.

Figures 9, 10, 11:
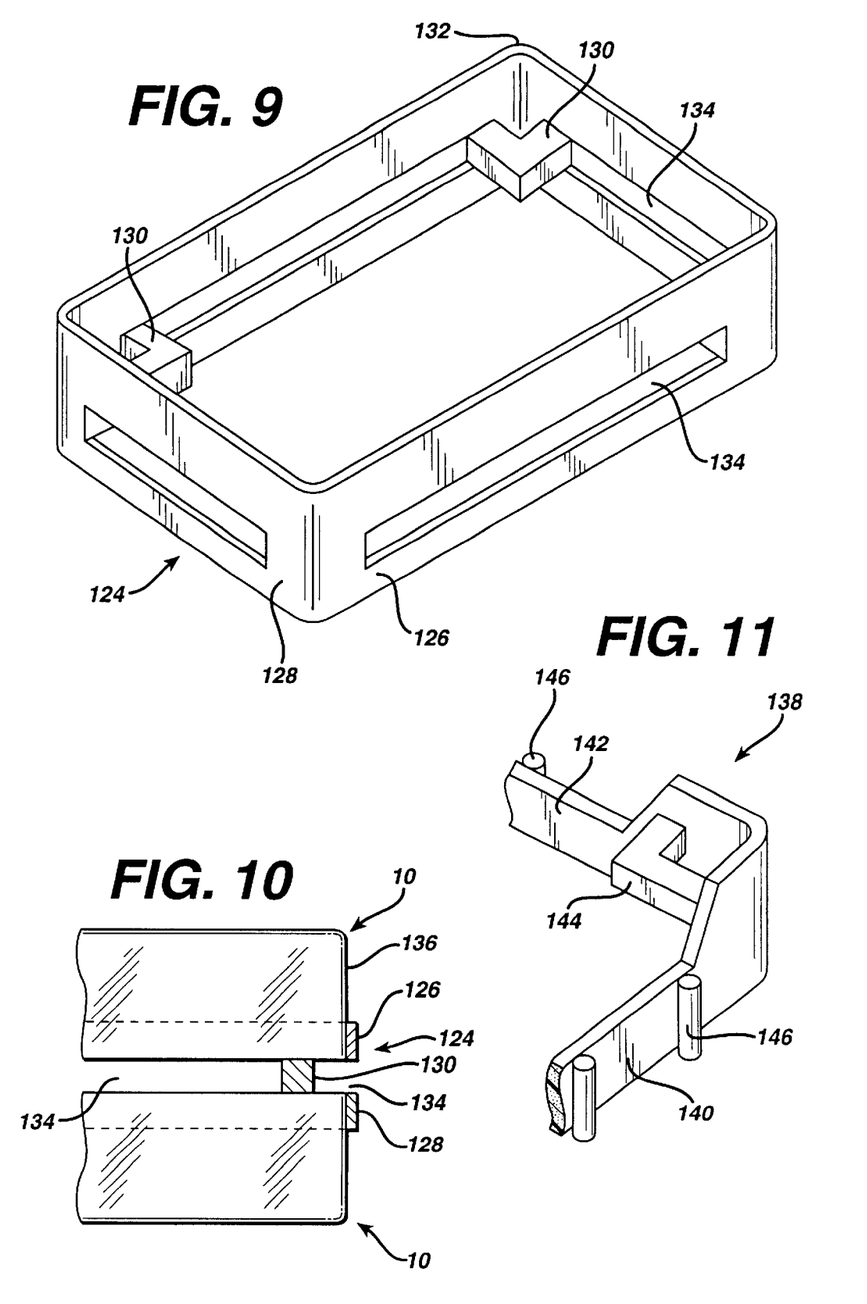
FIG. 9 is a perspective view of a stacking device according to the present invention.
FIG. 10 is a side view of the stacking device of FIG. 9 positioned between two sterilization containers to stack and separate the containers.
FIG. 11 is a perspective view of a further embodiment of a stacking device according to the present invention.

FIG. 9 illustrates a stacking device 124 for stacking sterilization trays 10 during a sterilization procedure. The stacking device 124 is rectangular in shape and of slightly larger dimensions and than the sterilization tray 10 (not shown in FIG. 9). It comprises vertical sidewalls 126 and vertical endwalls 128. An L-shaped shelf member 130 extends horizontally inwardly from each corner 132 of the stacking device 124. As illustrated in FIGS. 9 and 10, each of the sidewalls 126 and endwalls 128 has elongated openings 134 therethrough of similar vertical dimensions to the shelf member 130 so that when containers 10 are stacked using the stacking device 124, the flow of sterilizing gases into and out of the individual containers 10 is not impeded by the stacking device 124.

FIG. 10 shows two sterilization containers 10, each wrapped in a sterile wrap material 136. The stacking member 124 sits atop a first tray 10 with the shelf member 130 resting upon the tray 10. The second tray 10 rests upon the shelf member 130. Both trays 10 are positioned within the side and endwalls 126 and 128 of the stacking device. Thus, the two trays 10 are stacked and separated from each other with a full and open flow path thereabout.

FIG. 11 illustrates an alternative embodiment of a stacking device 138. In place of the opening 134, each of the side and endwalls 140 and 142 respectively have a low vertical profile vertically offset from a shelf member 144 to thereby provide an open flow path to the stacked trays (not shown in FIG. 11). Vertical ribs 146 on the side and endwalls 140 and 142 provide rigidity and maintain an open flow path, if the stacking device is placed next to another stacking device or flat surface.

Figure 12:
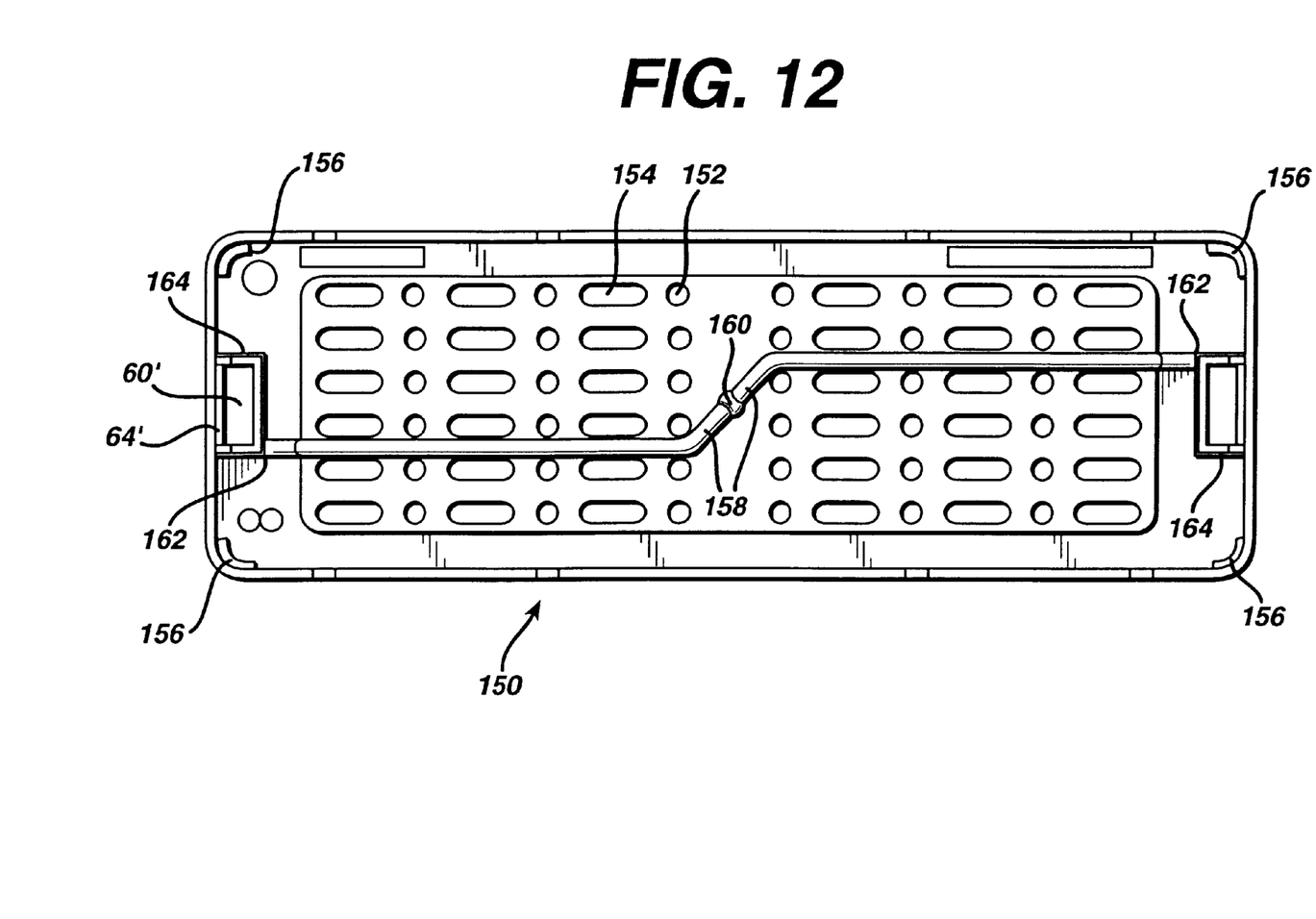
FIG. 12 is underside plan view of a further embodiment of a lid according to the present invention.

FIG. 12 illustrates an alternative embodiment of a lid 150 according to the invention. The lid 150 duplicates the lid 16 of FIGS. 1 and 3, with several modifications. Accordingly, features similar to those on the lid 16 will be designated with similar numerals with the addition of a single prime symbol ('). Specifically, the lid 150 differs from the lid 16 in its mixture of round and elongated apertures 152 and 154 respectively. Also, an additional fillet 156 has been added at each corner which both strengthens the lid 150 aids in lifting the lid 150 above the base 8 (not shown in FIG. 12) for improved circulation.

Liquid crystal polymers are known for their difficulty in molding. One particular problem arises where opposing flows of molten polymer meet. Such areas often have reduced strength and accordingly it is desirable to locate them away from areas of the molded article which will be subjected to high levels of stress. In the lid 150, the recess 60' is formed by a core pin in the mold (not shown). The molten polymer flows around the core pin and meets to enclose the recess 60'. Normally these flows would meet at the retaining lip 64'. However, this area is subjected to high stresses. Accordingly, the lid 150 is formed with a pair of flow leaders 158, each leading from a center area 160 of the lid 150 where the molten polymer is injected in the molding process and leading to an inside corner 162 of the respective recesses 60'. During the molding process the molten polymer thus flows around the core pin and the opposing flows meet at a side portion 164 of the recess 60'.

While the invention has been particularly described in connection with specific embodiments thereof, it is to be understood that this is by way of illustration and not of limitation, and that the scope of the appended claims should be construed as broadly as the prior art will permit.

I claim:

1. A sterilization container for sterilizing, transporting and storing instruments, comprising:

a tray having at least one port for passing sterilizing media into and out of the tray; means for holding a medical instrument within the tray, and an outer tray wall portion;

a lid, moveable with respect to the tray for providing access to the tray and having an outer lid wall portion;

a latching mechanism releasably connecting the lid to the tray; and a recessed portion in one of the tray outer wall portion and lid outer wall portion forming a latch recess, said latching mechanism being entirely received within said recess such that no portion of the latching mechanism extends laterally of the recess, whereby to reduce the chance that the latching mechanism might catch and puncture a thin protective glove of a user.

2. A sterilization container according to claim 1 wherein the latch recess further comprises opposing side walls and the latch mechanism further comprises:

an engagement surface located on the opposite of the tray outer wall portion and lid outer wall portion from that on which is located said latch recess; and a latch member rotatably mounted within the latch recess for rotation about an axis;

the latch member comprising an engagement lip engageable with the engagement surface and the latch member further comprising an actuation surface removed from said axis whereby a force applied to the actuation surface urges the latch member into rotation about the axis so as to move the engagement lip away from the engagement surface.

3. A sterilization container according to claim 2 wherein the latch member is positioned so that the force applied to the actuation surface is applied in a direction inwardly of the latch recess.

4. A sterilization container according to claim 3 wherein the latch member is rotatably mounted upon a torsion member extending inwardly of the latch recess from the opposing sidewalls, the torsion member biasing the latch member into a standing position about said axis.

5. A sterilization container according to claim 1 wherein the latch member has an outwardly facing portion facing out of the recess and an inwardly facing portion facing inwardly of the recess and wherein the engagement lip is disposed on the inwardly facing portion and wherein the outwardly facing portion is free of sharp edges.

6. A sterilization container for sterilizing, transporting and storing instruments, comprising:
- a tray having at least one port for passing sterilizing media into and out of the tray; means for holding a medical instrument within the tray, and an outer tray wall portion;
- a lid, moveable with respect to the tray for providing access to the tray and having an outer lid wall portion; and
- a latching mechanism releasably connecting the lid to the tray;
the improvement comprising:
- a latch recess formed in one of the tray outer wall portion and lid outer wall portion, said recess having opposing side walls;
- an engagement surface formed on the other of the tray outer wall portion and lid outer wall portion;
- a torsion member extending inwardly of the latch recess from the opposing sidewalls;
- a latch member supported on said torsion member, the latch member being rotatable about an axis and the torsion member biasing the latch member into a standing position about said axis; the latch member comprising an engagement lip engageable with the engagement surface and the latch member further comprising an actuation surface removed from said axis whereby a force applied to the actuation surface urges the latch member away from the engagement surface and the engagement lip away from the engagement surface.

7. A sterilization container according to claim 6 wherein the latch member has an outwardly facing portion facing out of the recess and an inwardly facing portion facing inwardly of the recess and wherein the engagement lip is disposed on the inwardly facing portion and wherein the outwardly facing portion is free of sharp edges.

8. A sterilization container according to claim 7 wherein the torsion member is formed of plastic.

9. A sterilization container according to claim 8 wherein the latch member, torsion member and the opposing sidewalls of the latch recess are integrally formed of plastic.

10. A sterilization container according to claim 6 wherein the latch recess is formed in the tray outer wall portion.

* * * * *